(12) United States Patent
Hartley et al.

(10) Patent No.: US 8,114,145 B2
(45) Date of Patent: Feb. 14, 2012

(54) TRIGGER WIRE SYSTEM

(75) Inventors: David Ernest Hartley, Wannanup (AU); Edward Graham Mills, Lutwyche (AU); Erik Edelboe Rasmussen, Slagelse (DK); Jens Vejby Schultz, Skovlunde (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/722,214

(22) Filed: Mar. 11, 2010

(65) Prior Publication Data

US 2010/0168838 A1    Jul. 1, 2010

Related U.S. Application Data

(62) Division of application No. 10/447,406, filed on May 29, 2003, now Pat. No. 7,803,177.

(60) Provisional application No. 60/392,682, filed on Jun. 28, 2002, provisional application No. 60/384,056, filed on May 29, 2002.

(51) Int. Cl.
*A61F 2/06* (2006.01)

(52) U.S. Cl. ....... 623/1.11; 606/108; 606/191; 606/192; 606/194; 606/198

(58) Field of Classification Search .................. 623/1.11
See application file for complete search history.

(56) References Cited

U.S. PATENT DOCUMENTS

| 4,913,141 | A | | 4/1990 | Hillstead ........................ 606/108 |
|---|---|---|---|---|
| 5,480,423 | A | * | 1/1996 | Ravenscroft et al. ......... 623/1.11 |
| 5,779,732 | A | * | 7/1998 | Amundson ................... 623/1.15 |
| 6,245,097 | B1 | | 6/2001 | Inoue ................................ 623/1 |
| 6,641,606 | B2 | | 11/2003 | Ouriel et al. ................. 623/1.12 |

* cited by examiner

*Primary Examiner* — Thomas J Sweet
*Assistant Examiner* — Christopher D Prone
(74) *Attorney, Agent, or Firm* — Brinks Hofer Gilson & Lione

(57) ABSTRACT

A prosthesis deployment device having a elongate catheter body and a trigger wire guide concentric about the elongate catheter body where the trigger wire guide comprises three trigger wire lumens separate and apart from a guide wire lumen, with three trigger wires being at least partially disposed in the three trigger wire lumens and configured to engage a portion of a prosthesis to retain the prosthesis adjacent to the trigger wire guide.

20 Claims, 7 Drawing Sheets

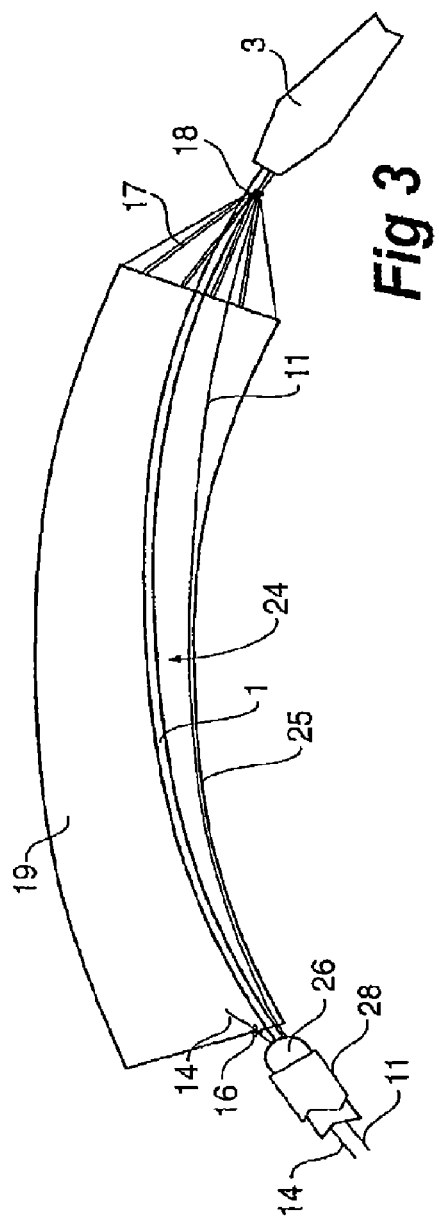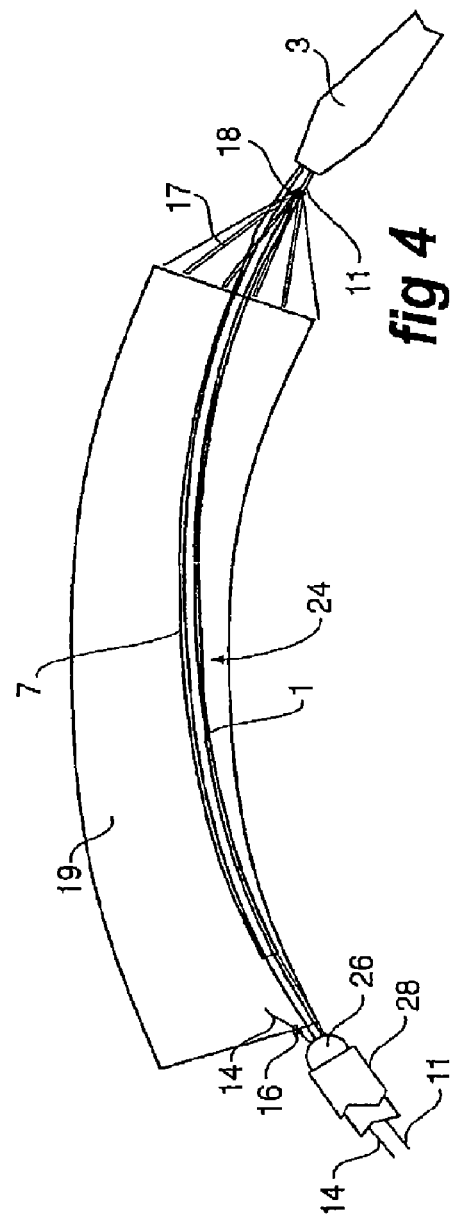

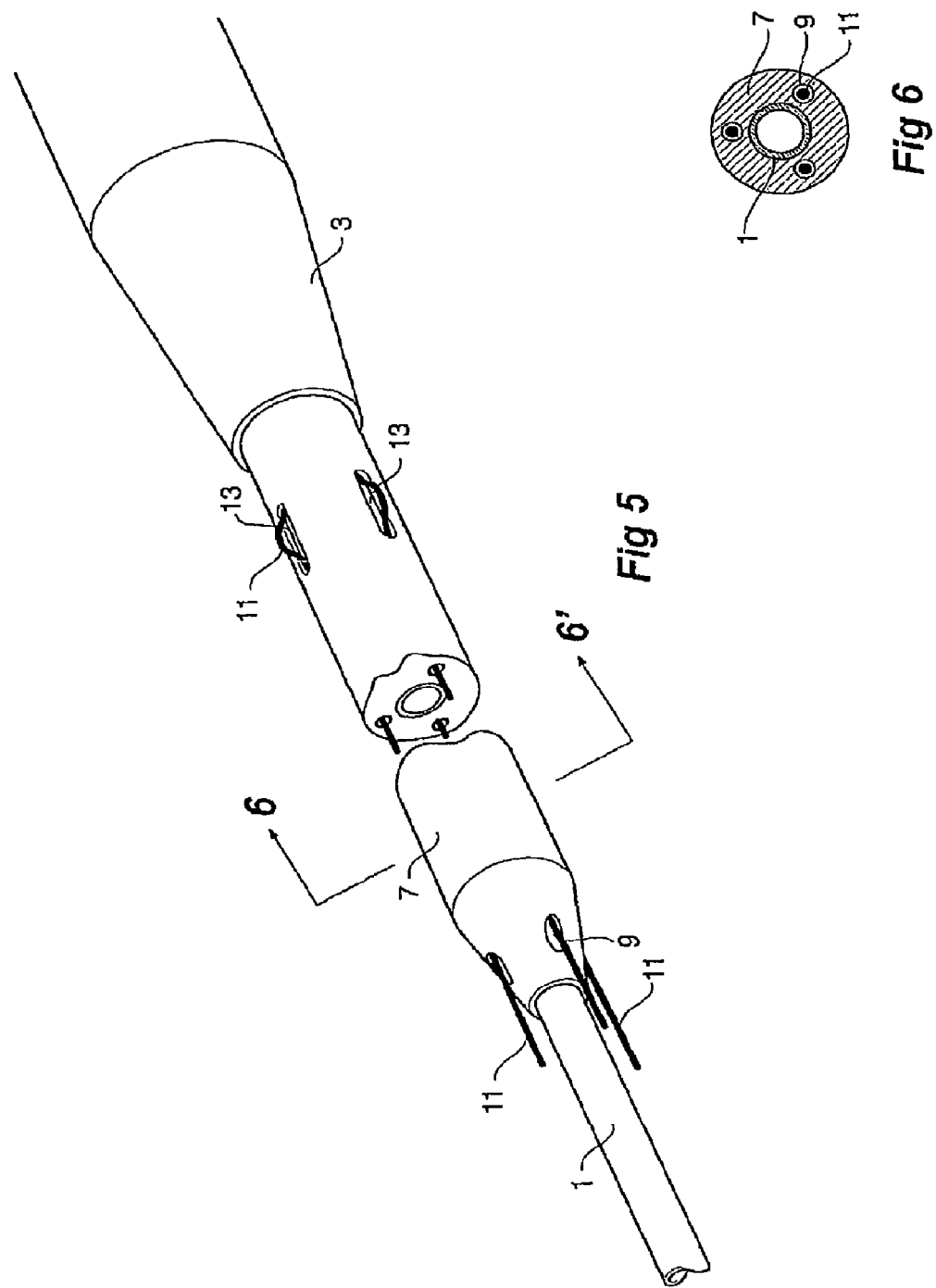

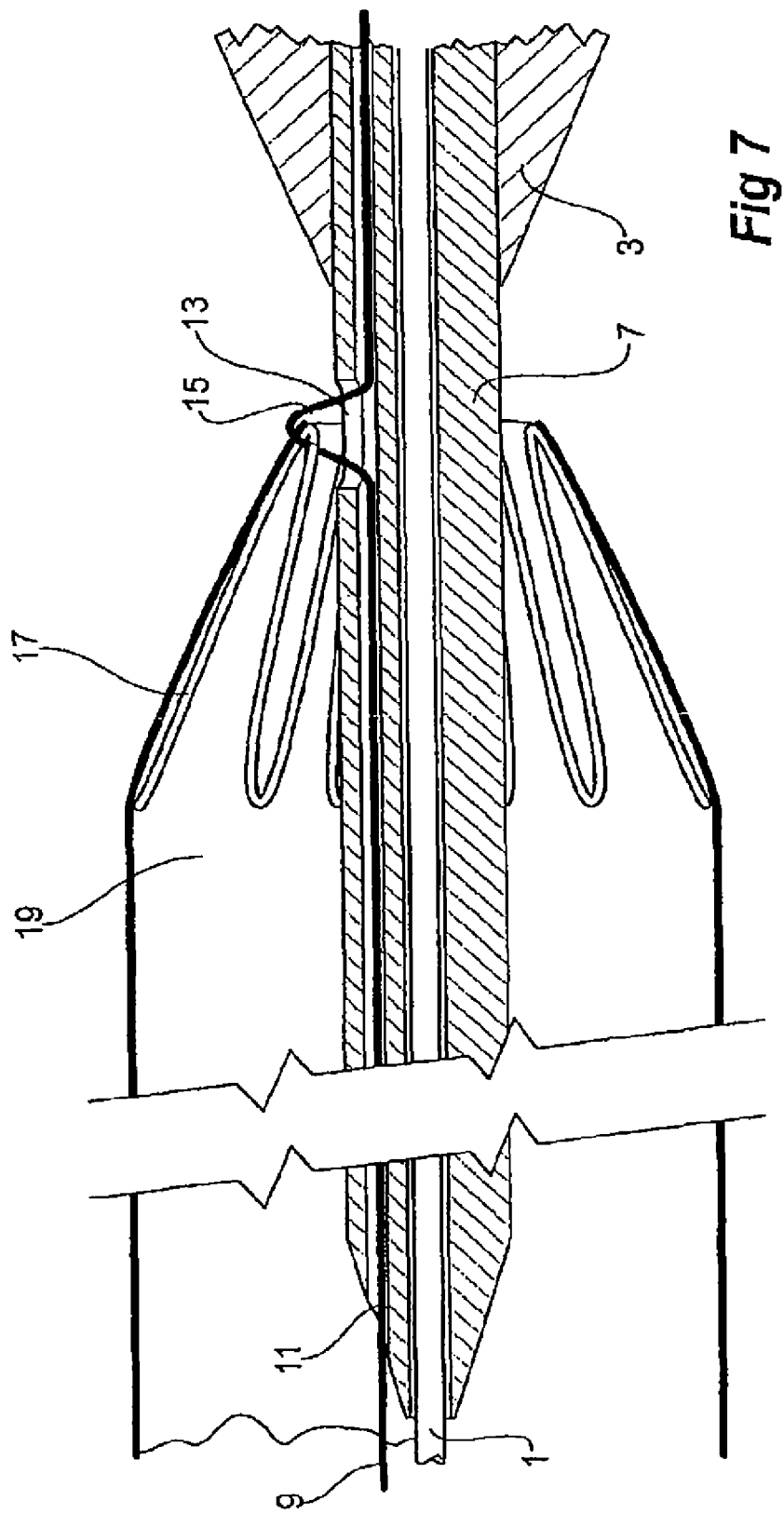

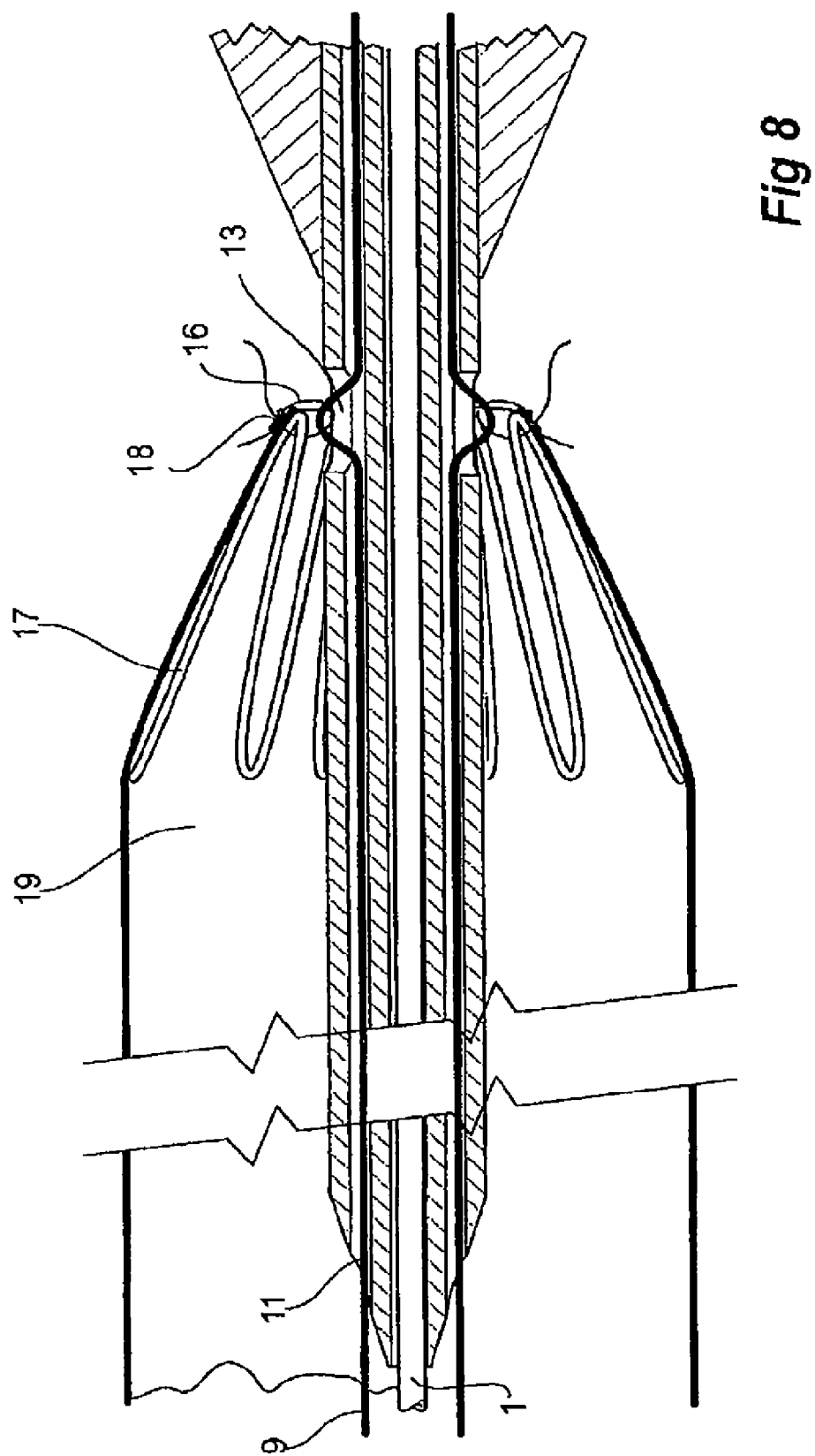

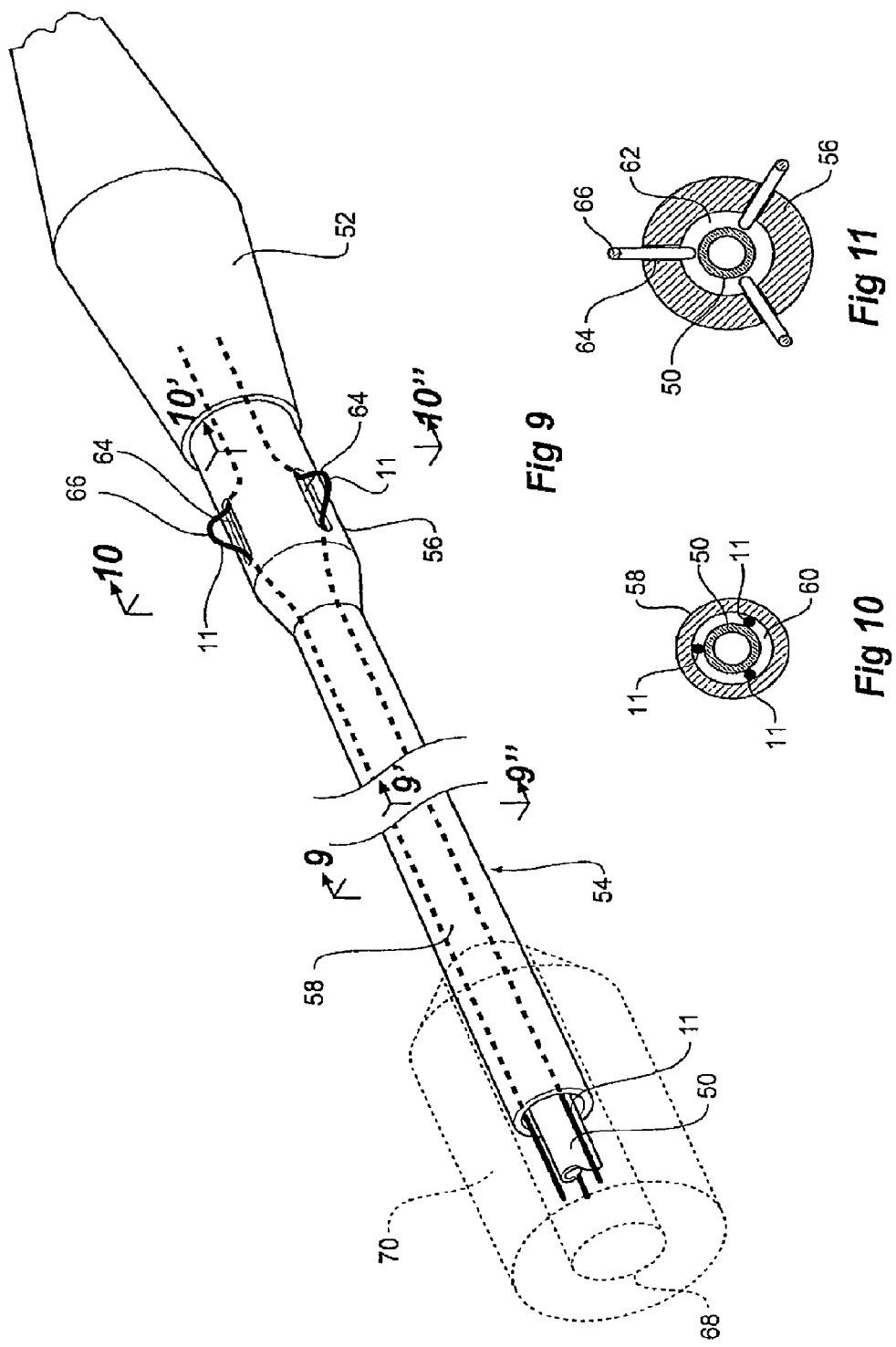

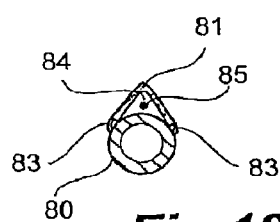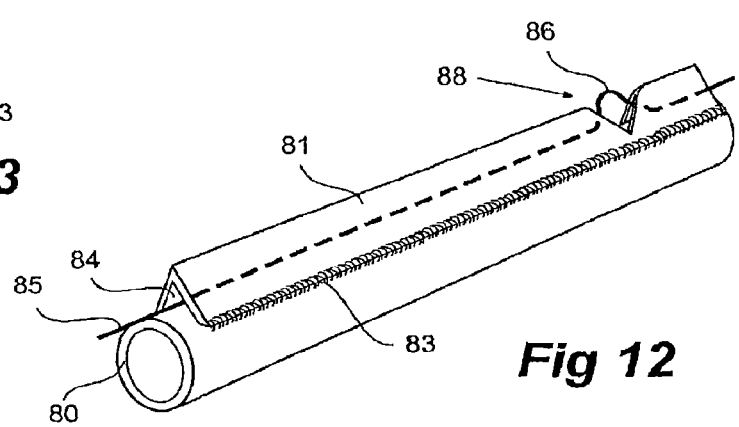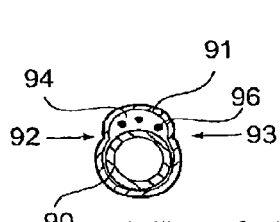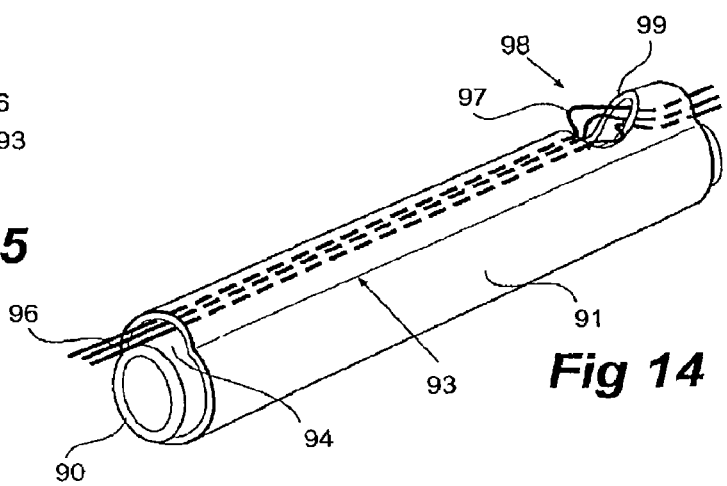

TRIGGER WIRE SYSTEM

CROSS REFERENCE TO RELATED APPLICATION

This application is a divisional of application Ser. No. 10/447,406 filed May 29, 2003, issued on Sep. 28, 2010 at U.S. Pat. No. 7,803,177 which claims priority to U.S. Provisional Application Serial No. 60/392,682, filed Jun. 28, 2002, and of the same title, and U.S. Provisional Application Serial No. 60/384,056, filed May 29, 2002, entitled "Multi-Piece Prosthesis Deployment Apparatus." All of the foregoing applications are hereby incorporated by reference.

BACKGROUND

This invention relates to a prosthesis deployment and more particularly to a trigger wire arrangement used on such devices to release a prosthesis when it is in a body lumen.

Deployment devices are used to deploy prostheses and in particular prostheses incorporating self expanding stents within lumens in the human body. This invention will generally be discussed in relation to the deployment of prostheses within the aorta but the invention is not so limited and may be used for other of deployment sites as well.

In some forms of deployment device trigger wires are used to retrain a prosthesis in a particular position on a deployment device or to retain self expanding stents of the prosthesis in a retracted state. In the region of the deployment device in which the prosthesis is carried, trigger wires can foul or catch with stents on the deployment device, particularly when the deployment device is bent to pass through convolutions in the lumen, therefore causing inaccurate deployment and perhaps jamming or breakage of the trigger wire.

Throughout this specification the term distal with respect to a prosthesis and a deployment device for prosthesis is the end of the prosthesis or deployment device which in use is furthest away in the direction of blood flow from the heart and the term proximal refers to the end of the prosthesis or deployment device which in use is nearest to the heart. When applied to other vessels corresponding terms such as caudal and cranial should be understood.

It is the object of this invention to provide an arrangement by which a trigger wire on a deployment device can be more safely routed to its destination or to at least provide a practitioner with a useful alternative.

BRIEF SUMMARY

In one form therefore, although this may not necessarily be the only or broadest form, the invention is said to reside in a trigger wire guide for a prosthesis deployment device, the prosthesis deployment device being of a type having a nose cone dilator located on a proximal end of the deployment device with an elongate catheter body coupled to the nose cone dilator with a guide wire lumen extending therethrough and a trigger wire guide concentric about the elongate catheter body that extends along at least a portion of the elongate catheter body, where the trigger wire guide comprises at least one trigger wire lumen formed within the trigger wire guide where the trigger wire lumen is separate and apart from the guide wire lumen and the trigger wire guide has an aperture, where at least one trigger wire is partially disposed within the at least one trigger wire lumen where the at least one trigger wire is configured to exit the aperture to engage the prosthesis, a stent of the prosthesis, or a suture retaining the prosthesis, and enter the same aperture to thereby retain a portion of the prosthesis adjacent to the trigger wire guide.

In an alternative embodiment, the invention comprises a prosthesis deployment device having a nose cone dilator with an elongate catheter body coupled to the nose cone dilator, the elongate catheter body having a guide wire lumen extending therethrough with a trigger wire guide concentric about the elongate catheter body and extending along at least a portion of the elongate catheter body, where the trigger wire guide comprises at least two trigger wire lumens formed within the trigger wire guide where each lumen is separate and apart from the guide wire lumen and at least two apertures in the trigger wire guide where at least one trigger wire is at least partially disposed within each of the at least two trigger wire lumens, where the at least two trigger wires are configured to exit each of the at least two apertures to engage the prosthesis, a stent of the prosthesis, or a suture retaining the prosthesis and enter the same aperture to thereby retain a portion of the prosthesis adjacent to the trigger wire guide.

In an alternative form the invention comprises a prosthesis deployment device comprising a nose cone dilator located on a proximal end of the deployment device with an elongate catheter body coupled to the nose cone dilator with the elongate catheter body having a guide wire lumen extending therethrough with a trigger wire guide concentric about the elongate catheter body extending along at least a portion of the elongate catheter body with the trigger wire guide comprising an enlarged proximal portion adjacent to the nose cone dilator with a distal portion of increasing diameter transition to the enlarged proximal portion having a maximum outer diameter less than the outer diameter of the enlarged proximal portion and three trigger wire lumens formed within the trigger wire guide with each lumen being separate from the guide wire lumen and extending at least partially within the trigger wire guide with at least three apertures in the trigger wire guide and with three trigger wires extending through the trigger wire guide with one trigger wire being at least partially disposed within each lumen and configured to exit the aperture to engage the prosthesis, a stent of the prosthesis, or a suture retaining the prosthesis and enter the same aperture to thereby retain a portion of the prosthesis adjacent to the trigger wire guide.

PCT Patent Publication No. WO 98/53761 entitled "A Prosthesis and a Method of Deploying a Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Application Number PCT/US02/34348 entitled "Prostheses for Curved Lumens" discloses prostheses with arrangements for bending the prosthesis for placement into curved lumens. This feature and other features disclosed in PCT Patent Application No. PCT/US02/34348 could be used with the present invention and the disclosure of PCT Patent Application No. PCT/US02/34348 is herewith incorporated in its entirety into this specification.

Australian Provisional Patent Application No. PS3215 entitled "A Stent-Graft Fastening Arrangement" discloses arrangements for fastening stents onto grafts particularly for exposed stents. This feature and other features disclosed in Australian Provisional Patent Application Number No. PS3215 could be used with the present invention and the disclosure of Australian Provisional Patent Application Number No. PS3215 is herewith incorporated in its entirety into this specification.

Australian Provisional Patent Application No. PR9617 entitled "Improving Graft Adhesion" discloses arrangements on stent grafts for enhancing the adhesion of such stent grafts into walls of vessels in which they are deployed. This feature and other features disclosed in Australian Provisional Patent Application Number No. PR9617 could be used with the present invention and the disclosure of Australian Provisional Patent Application No. PR9617 is herewith incorporated in its entirety into this specification.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Stent Barb" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting, replacing, and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

Australian Provisional Patent Application No. PS3243 entitled "Thoracic Deployment Device" discloses introducer devices adapted for deployment of stent grafts particularly in the thoracic arch. This feature and other features disclosed in Australian Provisional Patent Application Number No. PS3243 could be used with the present invention and the disclosure of Australian Provisional Patent Application Number No. PS3243 is herewith incorporated in its entirety into this specification.

Australian Provisional Patent Application No. 2002950951 entitled "Asymmetric Stent Graft Attachment" discloses retention arrangements for retaining onto and releasing prostheses from introducer devices. This feature and other features disclosed in Australian Provisional Patent Application Number No. 2002950951 could be used with the present invention and the disclosure of Australian Provisional Patent Application Number No. 2002950951 is herewith incorporated in its entirety into this specification.

BRIEF DESCRIPTION OF THE DRAWINGS

This then generally describes the invention but to assist with understanding, reference will now be made to the accompanying drawings which show preferred embodiments of the invention.

In the drawings:

FIG. 3 shows schematically the problem to which the present invention is directed;

FIG. 4 shows schematically how the problem is overcome by the use of a trigger wire guide according to one embodiment of the invention;

FIG. 5 shows a detail of part of the deployment device incorporating the trigger wire guide of one embodiment of the present invention;

FIG. 6 shows a transverse cross section of the guide along the line 6-6' shown in FIG. 5;

FIG. 7 shows a cross sectional view of a deployment device incorporating a trigger wire guide of the present invention retaining self expanding stents of a prosthesis;

FIG. 8 shows a similar view to FIG. 7 but with a different method of retaining the self expanding stents of the prosthesis;

FIG. 9 shows a detail of part of a deployment device incorporating the trigger guide wire of an alternative embodiment of the present invention;

FIG. 10 shows a cross-sectional view of the embodiment shown at FIG. 9 at the region 10, 10', 10";

FIG. 11 shows a cross-sectional view of the embodiment shown in FIG. 9 at the region 11, 11', 11";

FIG. 12 shows a detail of part of a deployment device incorporating the trigger guide wire of a further alternative embodiment of the present invention;

FIG. 13 shows a cross sectional view of the embodiment shown in FIG. 12;

FIG. 14 shows a detail of part of a deployment device incorporating the trigger guide wire of a further alternative embodiment of the present invention; and FIG. 15 shows a cross sectional view of the embodiment shown in FIG. 14.

DETAILED DESCRIPTION OF THE DRAWINGS AND THE PRESENTLY PREFERRED EMBODIMENTS

Figure 1:
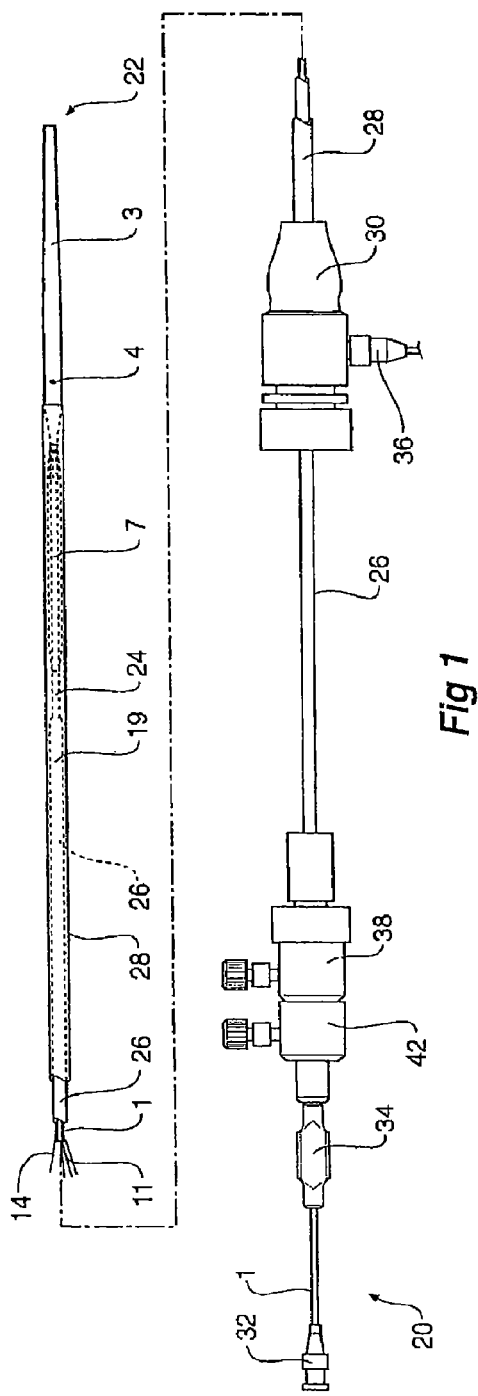
FIG. 1 shows a typical deployment device incorporating a trigger wire guide of the present invention in the ready to deploy state.
Figure 2:
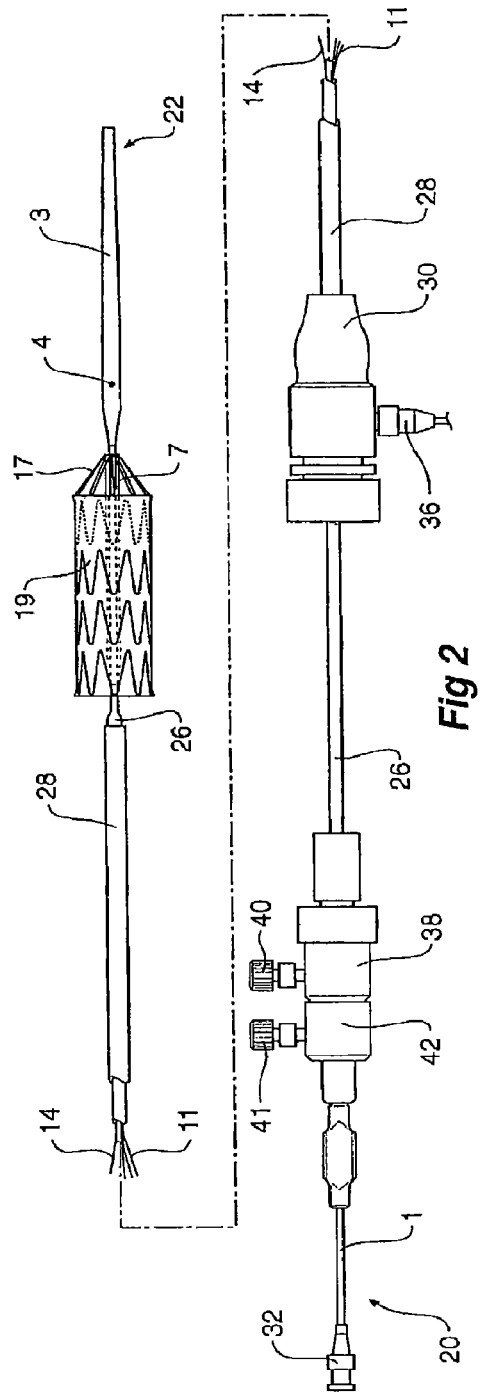
FIG. 2 shows the embodiment in FIG. 1 with a prosthesis partially deployed.

Now looking more closely to the drawings and in particular the embodiment shown in FIGS. 1 and 2, there is shown a prosthesis deployment device upon which the trigger wire guide of the present invention may be used.

The prosthesis deployment device of this invention comprises a guide wire catheter 1 extending between a distal end 20 and a proximal end 22 of the deployment device. In use the distal end 20 is adapted to remain outside the body of a patient and the proximal end 22 with its nose cone dilator 3 is adapted in use to be inserted into the arteries of a patient such as for treatment of an aortic aneurism. For such a treatment the deployment device is inserted through an incision into the femoral artery and through the iliac arteries to the aorta. The deployment device is usually deployed over a guide wire (not shown). There is a recess 24 between the nose cone dilator 3 and catheter body 26. The recess 24 is adapted to retain a prosthesis 19 in a compressed state with a sheath 28 extending from a sheath termination point 30 to the nose cone dilator 3 and assisting in holding the prosthesis in the compressed state. The hollow guide wire catheter 1 extends from a distal syringe attachment point 32 to the nose cone dilator so that manipulation of the guide wire catheter with respect to the catheter body 26 will move the nose cone dilator with respect to the catheter body. Manipulation can be either rotational or longitudinal movement.

A pin vice 34 at the distal end of the deployment catheter 26 locks the position of the guide wire catheter 1 with respect to the deployment catheter 26.

The deployment catheter 26 is surrounded by the sheath 28 extending from the sheath termination point 30 on the deployment catheter forward to the nose cone dilator 3. The sheath termination 30 includes a side tube 36 which has a hypodermic syringe attachment point (not shown) so that angiographic contrast fluids can be supplied into the sheath termination to travel between the sheath 28 and the catheter body 1.

The hypodermic syringe attachment point 32 at the distal end of the guide wire catheter is adapted for the supply of contrast angiographic fluid through the guide wire catheter to the nose cone dilator where it is adapted to be ejected through ports 4 in the sides of the nose cone dilator 3.

A trigger wire arrangement which incorporates three trigger wires 11 as will be discussed in relation to the embodiment shown in FIG. 5, for instance, extends from a trigger wire release mechanism 42 and then the trigger wires extend between the deployment catheter 26 and the guide wire catheter 1 and then through the recess 24 to the proximal end of the prosthesis 19. After the guide wires exit from the lumen between the central catheter 26 and the guide wire catheter 1 into the recess 24 they enter the trigger wire guide 7 until they exit through the aperture 13 (FIG. 5) thereby preventing fouling of the trigger wires with a prosthesis which is held retained by the sheath 28. The trigger wire release mechanism 42 has a thumb screw 41 which can be rotated to release the release mechanism to enable withdrawal of the three trigger wires 11.

Another trigger wire 14 is deployed between the guide wire catheter 1 and the catheter body 26 and extends from a trigger wire release mechanism 38 to the distal end of the prosthesis 19 where the distal end of the prosthesis 19 is retained to the trigger wire 14 by a mooring loop 18. The trigger wire release mechanism 38 has thumb screw 40 which can be rotated to release the trigger wire retention mechanism to withdraw the distal trigger wire 14 and hence release the distal mooring loop 18 to free the distal end of the prosthesis 19.

As shown in FIG. 2 the sheath 28 has been withdrawn by moving the sheath termination point 30 towards the distal end 20 of the prosthesis deployment device until the prosthesis 19 has been fully deployed except that at the proximal end the stents 17 are still retained by the loop 15 of trigger wire 11 (see FIG. 7). The distal component of the trigger wire release mechanism 38 and mooring loop 18 also retains the distal end of the prosthesis 19. The proximal end can be deployed, when the nose cone dilator has been manipulated so that the graft is in the correct position, by removal of the trigger wire 11 by actuation of the proximal trigger wire release mechanism 42 and then subsequently the distal end of the prosthesis 19 can be released by removal of the trigger wire 14 by actuation of the trigger wire release mechanism 38. For some situations it may be preferable to release the distal end of the stent graft before the proximal end and in such a situation the distal trigger wire release mechanism 38 and the proximal trigger wire release mechanism 42 would be mounted in the opposite order.

FIG. 3 shows schematically the problem to which the present invention is directed and FIG. 4 shows schematically how the problem is overcome by the use of a trigger wire guide according to one embodiment of the invention. The prosthesis deployment device is shown in a more realistic configuration as it would be in a curved lumen of a patient such as the thoracic arch of the patient at the stage of deployment as shown in FIG. 2.

As shown in FIG. 3, without the trigger wire guide of the present invention, the trigger wire or wires 11 extend from the lumen between the guide wire catheter 1 and the deployment catheter body 26 to a proximal mooring loop 18 for the prosthesis 19. The proximal mooring loop 18 retains the exposed stents 17 adjacent the nose cone dilator 3 in a retracted condition. The guide wire does not follow, however, the curve of the guide wire catheter 1 but goes in a more straight line and in doing so fouls with the wall 25 of the prosthesis 19 and can be more difficult to withdraw when required and in serious cases can tangle with stents associated with the prosthesis and jam or break.

The problem is solved as shown in FIG. 4 with the use of a trigger wire guide 7 extending along that portion of the guide wire catheter 1 which is within the recess 24. By this arrangement the trigger wire 11 cannot foul with the prosthesis 19.

In FIGS. 5 to 7 a part of the prosthesis deployment device is shown and includes the guide wire catheter 1 which extends the length of the deployment device and at the proximal end of the guide wire catheter 1 is the nose cone dilator 3.

Extending back from the nose cone dilator 3 and surrounding the guide wire catheter 1 is a trigger wire guide 7. The trigger wire guide 7 is coaxial with the guide wire catheter 1 and includes three lumens 9 through which, in use, pass trigger wires 11.

Just distal of the nose cone dilator 3 there are apertures 13 in the trigger wire guide 7 extending into each lumen 9 and out of which aperture 13 extends the guide wire 11 in a loop 15 so that it can engage the zig zag stents 17 of a prosthesis 19 (see FIG. 7). The trigger wire 11 continues along the lumen 9 to terminate within the region of the nose cone dilator 3. When it is desired to release the stent 17, the trigger wire 11 is pulled out as is discussed in relation to FIGS. 1 and 2.

The prosthesis is also shown in FIG. 7. In this embodiment the proximal stent 17 of the prosthesis 19 is a covered stent whereas in FIG. 2 an uncovered proximal stent is shown. The principle of retention using the trigger wire 11 is the same however, except that in FIG. 7, the trigger wire 11 in its loop 15 passes through the graft material as well.

As an alternative to the use of the loop 15 to engage directly into the stent and graft material the arrangement as shown in FIG. 8 can be used. In FIG. 8 a piece of thread 16 such as a monofilament or woven suture material is used with a loop around the trigger wire 11, the stent 17 and the graft material of the prosthesis 19 with a knot or a mooring loop 18. The stent 17 and the graft material of the prosthesis 19 are released from the trigger wire 11 when the trigger wire is withdrawn. In such a situation the loop of thread 16 would stay attached to the stent 17 or the graft material of the prosthesis 19.

In the embodiment shown in FIGS. 9, 10 and 11, it will be seen that a deployment device according to this embodiment includes a guide wire catheter 50 which extends along the length of the deployment device and at the proximal end of the guide wire catheter 50 is a nose cone dilator 52. Extending back from the nose cone dilator and surrounding the guide wire catheter is a trigger wire guide generally shown as 54. The trigger wire guide 54 is coaxial with the guide wire catheter 50 and includes an enlarged portion generally shown as 56 and a thinner tubular portion 58. In the region of the tubular portion 58 there is an annular lumen between the guide wire catheter 50 and the tubular portion 58 through which the trigger wire or wires 11 pass.

In the region 56 adjacent the nose cone dilator 52 the trigger wires extend from a central annular lumen 62 which is continuous with the lumen 60 and then pass out through elongate apertures 64 in the form of a loop 66 and then continue on through the lumen 62. The loop 66 is adapted to engage a stent or graft material of a prosthesis to hold the proximal end of the prosthesis in a retracted or constrained condition until it is desired to release it. Alternatively the trigger wire 1 can engage a suture tied to a stent of a prosthesis to hold it in a retracted or constrained condition until it is desired to release it.

When it is desired to release the prosthesis the trigger wire 11 is pulled out as was discussed in relation to FIGS. 4 and 5.

In this embodiment of the deployment device the tubular portion 58 extends back into the lumen 68 of the deployment catheter 70 so that no portion of the guide wire would be visible in the region of the deployment device into which the stent graft or prosthesis is received in use.

FIG. 12 shows a detail of part of a deployment device incorporating the trigger guide wire of a further alternative embodiment of the present invention and FIG. 13 shows a cross sectional view of the embodiment shown in FIG. 12.

In this embodiment the guide wire catheter 80 of the deployment device has soldered or otherwise fastened along at least a part of its length an inverted V shape cross section component 82 which with the guide wire catheter defines a lumen 84 between them. In this case solder 83 is used to fasten the V shape cross section component 82 to the guide wire catheter. A trigger wire 85 can pass along the lumen 84 and exit in a loop 86 in the region 88 where the V shape cross section component 81 is not present. The loop 86 can engage a stent of a prosthesis to hold the stent until it is desired to release it or to engage a suture tied to a stent of a prosthesis.

FIG. 14 shows a detail of part of a deployment device incorporating the trigger guide wire of a further alternative embodiment of the present invention and FIG. 15 shows a cross sectional view of the embodiment shown in FIG. 14.

In this embodiment the guide wire catheter 90 of the deployment device has a concentric metal tube 91 placed around it and crimped at points 92 and 93 to the guide wire catheter 90 to clamp it to the catheter and thereby with the guide wire catheter defining a lumen 94 for the passage of trigger wires. In this case there are three trigger wires but there could be only a single trigger wire or other configuration of trigger wires. The trigger wires 96 can pass along the lumen 94 and exit in loops 97 in the region 98 where there is a cut-out 99 in the crimped tube 91. The loops 97 can engage a stent of a prosthesis to hold the stent until it is desired to release it or to engage a suture tied to a stent of a prosthesis.

Throughout this specification various indications have been given as to the scope of this invention but the invention is not limited to any one of these but may reside in two or more of these combined together. The examples are given for illustration only and not for limitation.

Throughout this specification unless the context requires otherwise the words comprise and include and variations such as comprising and including will be understood to imply the inclusion of a stated integer or group of integers but not the exclusion of any other integer or group of integers.

What is claimed is:

1. A prosthesis deployment device comprising:
a nose cone dilator located on a proximal end of the deployment device;
an elongate catheter body coupled to the nose cone dilator, the elongate catheter body having a guide wire lumen extending therethrough;
a trigger wire guide concentric about the elongate catheter body and extending along at least a portion of the elongate catheter body, the trigger wire guide comprising:
an enlarged proximal portion adjacent to the nose cone dilator;
a distal portion of increasing diameter transitioning to the enlarged proximal portion having a maximum outer diameter less than the outer diameter of the enlarged proximal portion;
at least one trigger wire lumen formed within the trigger wire guide, the at least one trigger wire lumen separate and apart from the guide wire lumen; and
an aperture in the least one trigger wire guide; and
at least one trigger wire at least partially disposed within the at least one trigger wire lumen, the at least one trigger wire configured to exit the aperture to engage the prosthesis, a stent of the prosthesis, or a suture retaining the prosthesis, and enter the same aperture to thereby retain a portion of the prosthesis adjacent to the trigger wire guide.

2. The prosthesis deployment device of claim 1 wherein the trigger wire guide is coaxial with the guide wire catheter.

3. The prosthesis deployment device of claim 1 wherein a proximal portion of the trigger wire guide has a substantially constant diameter.

4. The prosthesis deployment device of claim 3 wherein the aperture is formed within the proximal portion of the trigger wire guide.

5. The prosthesis deployment device of claim 1 wherein the at least one trigger wire lumen comprises at least two trigger wire lumens that are equidistantly located from one another within the trigger wire guide.

6. The prosthesis deployment device of claim 5 wherein the trigger wire guide is radially fixed relative to the guide wire catheter.

7. The prosthesis deployment device of claim 6 wherein the trigger wire guide extends only partially along a proximal portion of the guide wire catheter.

8. The prosthesis deployment device of claim 7 wherein the diameter of each of the at least two trigger wire lumens is less than the diameter of the guide wire lumen.

9. The prosthesis deployment device of claim 8 wherein the proximal portion has a substantially constant diameter.

10. A prosthesis deployment device comprising:
a nose cone dilator located on a proximal end of the deployment device;
an elongate catheter body coupled to the nose cone dilator, the elongate catheter body having a guide wire lumen extending therethrough;
a trigger wire guide concentric about the elongate catheter body and extending along at least a portion of the elongate catheter body, the trigger wire guide comprising:
an enlarged proximal portion adjacent to the nose cone dilator;
a distal portion of increasing diameter transitioning to the enlarged proximal portion having a maximum outer diameter less than the outer diameter of the enlarged proximal portion;
at least two trigger wire lumens formed within the trigger wire guide, each lumen separate and apart from the guide wire lumen; and
at least two apertures in the trigger wire guide; and
at least one trigger wire being at least partially disposed within each of the at least two trigger wire lumens and configured to exit each of the at least two apertures to engage the prosthesis, a stent of the prosthesis, or a suture retaining the prosthesis, and enter the same aperture to thereby retain a portion of the prosthesis adjacent to the trigger wire guide.

11. The prosthesis deployment device of claim 10 wherein the trigger wire guide is coaxial with the guide wire catheter.

12. The prosthesis deployment device of claim 11 wherein the at least two trigger wire lumens comprises three trigger wire lumens that are spaced equidistantly from one another within the trigger wire guide.

13. The prosthesis deployment device of claim 12 wherein the diameter of each of the three trigger wire lumens is less than the diameter of the guide wire lumen.

14. The prosthesis deployment device of claim 10 wherein the guide wire catheter is separate and apart from the trigger wire guide.

15. The prosthesis deployment device of claim 14 wherein the enlarged proximal portion of the trigger wire guide has a substantially constant diameter.

16. The prosthesis deployment device of claim 15 wherein the aperture in each of the at least two trigger wire lumens is formed along the enlarged proximal portion of the trigger wire guide.

17. A prosthesis deployment device comprising:
- a nose cone dilator located on a proximal end of the deployment device;
- an elongate catheter body coupled to the nose cone dilator, the elongate catheter body having a guide wire lumen extending therethrough;
- a trigger wire guide concentric about the elongate catheter body extending along at least a portion of the elongate catheter body, the trigger wire guide comprising:
  - an enlarged proximal portion adjacent to the nose cone dilator;
  - a distal portion of increasing diameter transitioning to the enlarged proximal portion having a maximum outer diameter less than the outer diameter of the enlarged proximal portion;
  - three trigger wire lumens formed within the trigger wire guide, each trigger wire lumen being separate from the guide wire lumen and extending at least partially within the trigger wire guide; and
  - at least one aperture in the least one trigger wire guide; and
- three trigger wires extending through the trigger wire guide, one trigger wire being at least partially disposed within each lumen and configured to exit each aperture to engage the prosthesis, a stent of the prosthesis, or a suture retaining the prosthesis and enter the same aperture to thereby retain a portion of the prosthesis adjacent to the trigger wire guide.

18. The prosthesis deployment device of claim 17 wherein the three trigger wire lumens are spaced equidistantly from one another within the trigger wire guide.

19. The prosthesis deployment device of claim 17 wherein each of the diameters of each of the three trigger wire lumens is less than the diameter of the guide wire lumen.

20. The prosthesis deployment device of claim 19 wherein the apertures for each of the three trigger wire lumens is formed along the enlarged portion of the guide wire catheter.

* * * * *

UNITED STATES PATENT AND TRADEMARK OFFICE
CERTIFICATE OF CORRECTION

PATENT NO. : 8,114,145 B2
APPLICATION NO. : 12/722214
DATED : February 14, 2012
INVENTOR(S) : David Ernest Hartley et al.

It is certified that error appears in the above-identified patent and that said Letters Patent is hereby corrected as shown below:

In the Claims

In column 7, claim 1, line 67, after "aperture in the" insert --at--.

In column 10, claim 17, line 5, after "aperture in the" insert --at--.

Signed and Sealed this
Twenty-third Day of April, 2013

Teresa Stanek Rea
*Acting Director of the United States Patent and Trademark Office*